United States Patent [19]
Pol et al.

[11] Patent Number: 5,271,746
[45] Date of Patent: Dec. 21, 1993

[54] IMPLANTABLE BLOOD PUMP WITH INEXTENSIBLE DEFORMABLE CLOSED BAG

[75] Inventors: Vincent Pol, Marseilles; Jean-Claude Dumas, Auriol, both of France

[73] Assignee: Clinique de la Residence du Parc, France

[21] Appl. No.: 853,136

[22] Filed: Mar. 18, 1992

[30] Foreign Application Priority Data

Mar. 20, 1991 [FR] France ............................. 91 03386

[51] Int. Cl.$^5$ ............................................... A61M 1/12
[52] U.S. Cl. ............................................. 623/3; 600/16
[58] Field of Search ................ 600/16, 17, 18; 623/3, 623/12; 128/DIG. 24

[56] References Cited

U.S. PATENT DOCUMENTS

| | | | |
|---|---|---|---|
| 4,750,903 | 6/1988 | Cheng | 623/3 |
| 4,902,291 | 2/1990 | Kolff | 600/16 |
| 4,976,729 | 12/1990 | Holfert et al. | 623/3 |

FOREIGN PATENT DOCUMENTS 0148661 8/1985 European Pat. Off. .

Primary Examiner—William E. Kamm
Assistant Examiner—Kennedy J. Schaetzle
Attorney, Agent, or Firm—Blakely, Sokoloff, Taylor & Zafman

[57] ABSTRACT

The invention relates to an implantable blood pump of the type comprising a shell, a closed deformable bag, an inlet valve and an outlet valve, a drum arranged to roll over a wall of the bag, a bracket mounted to rotate about the axis of the drum and connected by an inextensible flexible component to one of the end edges of the bag, and an electric motor integrated inside the drum and suitable for driving the bracket and the drum in mutual and antagonistic rotation over a fraction of a turn to compress the bag which winds onto the drum to expel blood fluid. According to the invention, the outer shell is rigid and constitutes a sealed housing in which the bag can deform, and the bag is made, at least in part, of a material that is inextensible in two directions so that its original volume remains constant, said bag thus being made insensitive to external underpressure tending to increase its volume while blood fluid is being expelled. The invention is applicable to making non-displacement peristaltic cardiac prosthesis.

15 Claims, 2 Drawing Sheets

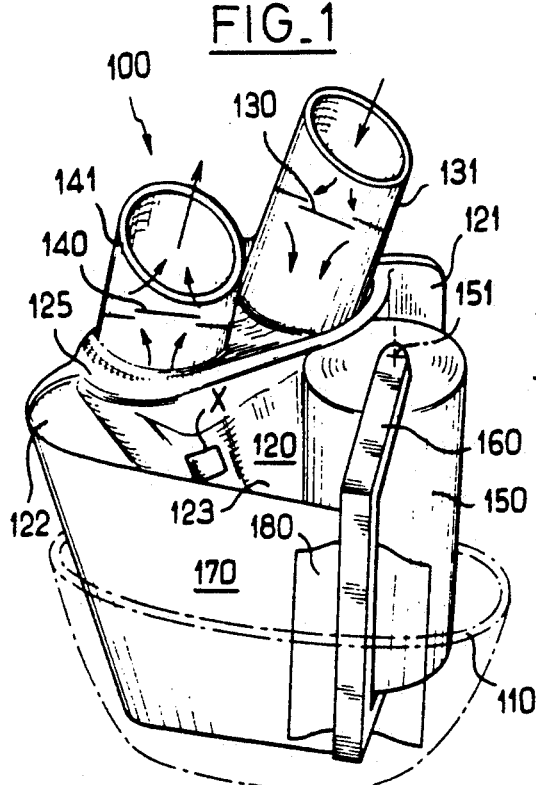
FIG_1
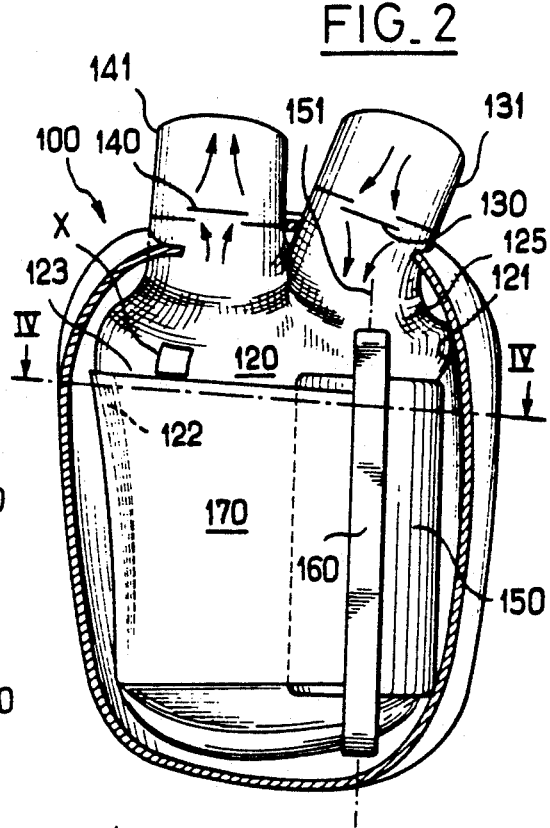
FIG_2
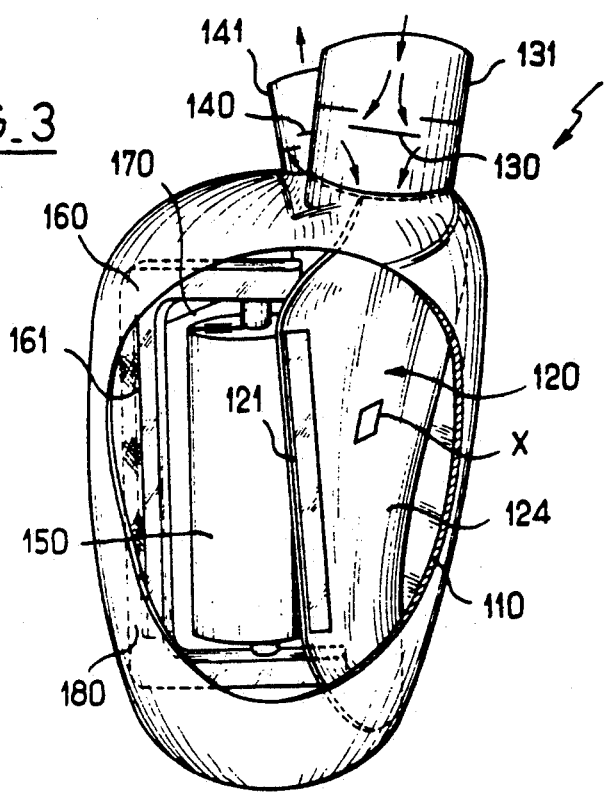
FIG_3

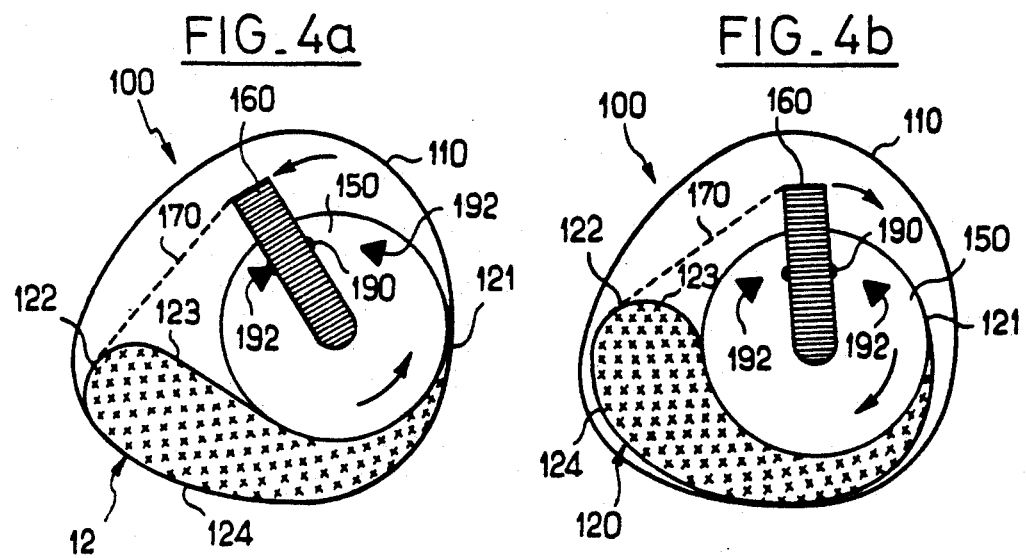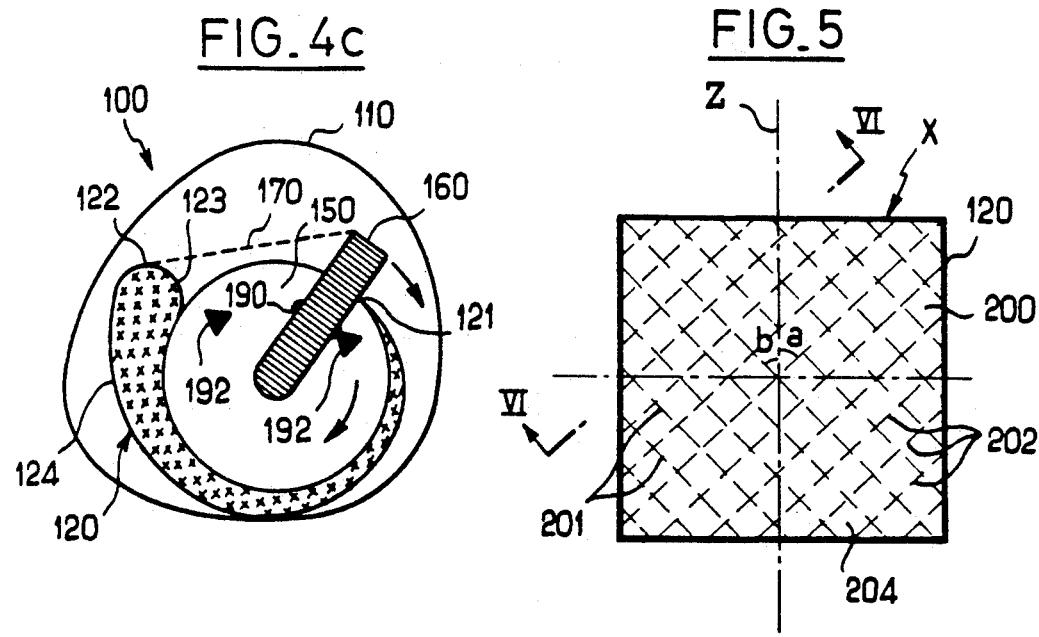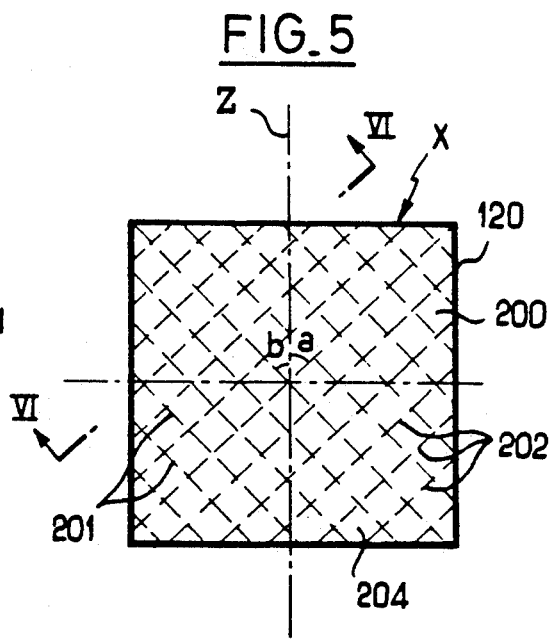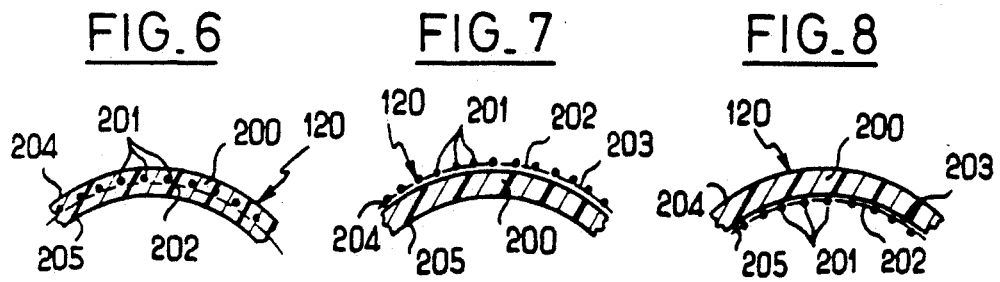

IMPLANTABLE BLOOD PUMP WITH INEXTENSIBLE DEFORMABLE CLOSED BAG

The invention relates to an implantable blood pump, and more particularly to a pump of the type comprising an outer shell, at least one essentially flat and deformable closed bag, said bag being disposed inside the shell and being connected to an inlet valve to enable it to be filled with blood fluid and to an outlet valve for delivering blood fluid, and drive means for compressing the closed bag in a determined sequence by applying external stress thereto.

BACKGROUND OF THE INVENTION

It thus constitutes a peristaltic type pump which is designed so that from the physiological point of view the behavior of the present pump is close to that of nature so as to avoid any hemolysis phenomenon (i.e. destruction of red corpuscles), and to reduce as far as possible shock phenomena due to sudden changes of pressure in the blood fluid. Insofar as possible, the design of the pump must also ensure that its operation is essentially non-displacement in order to avoid the risk of venous collapse.

Several systems have already been proposed for making a heart ventricular prosthesis.

Of the most recent implantable systems, mention may be made initially of the system including a closed flat bag having each of its two walls in contact with a respective presser plate for the purpose of compressing the bag to expel blood fluid therefrom. These two plates are hinged to the free ends of two levers that move apart from or towards each other like scissors blades, the opposite ends of the two levers being hinged on a common support and each lever supporting a respective solenoid in the vicinity of said common support. That assembly is described in particular in an article entitled "Implantable LVDA" by P. M. Portuer et. col. at pp. 115-141 of "Assisted Circulation—2" edited by Felix Unger, and published in 1984 by Springer-Verlag—Berlin, Heidelberg, New York, Tokyo.

The assembly constituted by the closed bag and the drive means for compressing the bag is disposed inside an essentially rigid outer shell serving both to make the implant comfortable and to protect the components of the prosthesis.

However, the use of a rigid and sealed outer shell gives rise to disturbances in the peristaltic operation of the pump, which disturbances can have consequences that are very severe for the patient since they run the risk of giving rise to venous collapse.

This results from the fact that the displacements of the volumes of blood in the closed bag give rise to pressure variations inside the rigid and sealed shell, such that the underpressure at the end of the ejection stage (delivering blood fluid) may reach a very high value.

For example, with a pump having a shell of 300 $cm^3$ and a closed bag capable of ejecting 40 $cm^3$ of blood fluid per systole, the bag is subjected at the end of the ejection stage to underpressure exceeding 70 mm of mercury (i.e. 9,100 Pa which is comparable to the ejection pressure), and which can even reach 100 mm of mercury (i.e. 13,000 Pa), which is a very high value if it is compared with the mean ejection pressure from a natural heart which is about 150 mm of mercury (i.e. 19,500 Pa).

In addition, such a system, whose operation is, substantially of the displacement type, does not make it possible to avoid this physical phenomenon of underpressure, unless, of course, a shell is provided that is of very large volume, but under such circumstances the pump would take up too much room.

U.S. Pat. No. 4,976,729 (Holfert et al.) and U.S. Pat. No. 4,750,903 (Cheng) describe pneumatic systems whose operation is disturbed little or not at all by underpressure in the shell. The underpressure is completely masked by the compression gas or the suction vacuum driving the membrane or the bag. In contrast, the driving energy requirements are increased to compensate the removal of blood. Such an increase is no problem in systems driven from outside the patient, which systems in any case present very low energy efficiency.

The Applicant has proposed an implantable system with non-displacement operation as described in detail in European patent No. 0 148 661.

That system comprises an implantable blood pump of the type comprising an outer shell, at least one essentially flat and deformable closed bag disposed inside the shell, having one of its walls in contact with the inside surface of said shell, and being connected to an inlet valve to enable it to be filled with blood fluid and to an outlet valve to enable it to deliver blood fluid, a cylindrical drum having an end-edge of the bag fixed to a generator line thereof and organized to roll over the other wall of said bag, a C-shaped bracket mounted to rotate about the axis of said drum and having its central portion connected by means of a flexible inextensible component to the other end edge of the bag, and an electric motor integrated within the drum having its stator secured to said drum and having its rotor driving said bracket, said motor enabling the bracket and the drum to be driven in mutual and antagonistic rotation through a fraction of a turn to compress the bag which winds onto said drum in order to expel the blood fluid.

The outer shell of the implantable pump described in the above-specified European patent is made of biocompatible material (e.g. silicone rubber or polyurethane) making it possible to associate the geometrically deformable shape of the shell with a material that has its own memory (using a material having its own geometrical memory improves energy restitution since the memory of the material is added to the deformation that results from the relative displacement of the drum and the C-shaped bracket).

Although the use of a flexible outer shell does indeed avoid the above-described phenomenon of underpressure, it suffers in practice from certain drawbacks: the movements of the motorized components are not always tolerated well by the adjacent organs, which constitutes a source of discomfort for the patient; in addition, even with perfect biocompatibility, in the long term rigid new tissue is observed to form on the outside of the shell, giving rise to increasing sensitivity to underpressure during the ejection stage. Furthermore, if the outer shell is too flexible, it may collapse during the movements of the motor-driven components, and in the limit it may jam the bracket.

It would naturally be most advantageous to be able to conserve the structural organization of that pump (in order to retain its non-displacement operation) while using an outer shell that is rigid and hermetically closed (in order to both ensure that the implant is comfortable and to protect the components of the prosthesis).

However, the underpressure physical phenomenon mentioned above for the preceding system is then encountered and it gives rise to a suction force on the closed bag during the ejection stage.

Whatever type of implantable system is used, there are numerous consequences of the underpressure phenomenon:

a considerable reduction in the volume of ejected blood fluid;

a drop in pressure towards the aorta; and too much energy is consumed by the drive system which must overcome the additional force.

If this physical phenomenon is to be countered, it is necessary to provide the implantable pump with a compensation system.

Several compensation systems may then be considered, and some have indeed been experimented with: the compensation may be rigid and internal, flexible and internal, or it may be external.

However, the following explanations show that such systems do not really give satisfaction.

Known rigid internal compensation systems include rated springs or electromagnets with pistons for moving at the appropriate moment a volume that enables the underpressure in the shell to be compensated.

Systems of this type have been experimented with, but they are not really workable at present. In addition to their large bulk, they suffer from the drawback of requiring mechanical or pneumatic coupling between the compensation volume and means for measuring of the underpressure in the shell, all of which must be placed in the patient's chest. In addition, such systems are not free from danger since the slightest tendency towards positive pressure (overcompensation) prevents the bag filling.

Known flexible internal compensation systems are based on the principle of a special in-body flexible bag whose volume is necessarily large. Such systems are not suitable since the special bag rapidly becomes the seat of rigid new tissue formation: the special compensation bag then progressively looses its ability to deform, and ends up by becoming an additional dead volume like the shell. In any event, the real compensation that could be expected is highly limited from the beginning because of the equilibrium that is established quickly (the system behaves like a closed system).

There then remains the solution of external compensation which remains theoretically possible: if the sealed shell remains at atmospheric pressure via a tube enabling it to "breathe", then system performance returns to that of an open shell. However, this solution requires the use of a transcutaneous catheter which constitutes a path for infection, particularly if the implant is for the long term. In addition, if the implant is completely internal, including its source of energy, such a catheter quickly becomes unacceptable to the patient.

In a variant, attempts have been made to use a catheter with a syringe for creating a small amount of underpressure, but in practice such a solution is hardly any more satisfactory.

Finally, known compensation systems do not make it possible to counter the physical underpressure phenomenon in satisfactory manner when a rigid and sealed shell is used, such that present solutions remain limited to comprises between these systems without real progress.

It is of interest to observe that most specialists, when faced with the need to provide a compensation system, have sought to reduce the dead volume of the shell. However, it appears that such an approach is not suitable since if the volume of the shell is halved, then the underpressure is substantially doubled during ejection, such that the force applied on the motor system becomes very large and all of the unrestrained portions of the flexible bag start to inflate, thereby reducing the ejected volume correspondingly. It is clear that it is impossible to avoid having such unrestrained portions, particularly where the flexible bag is connected to the inlet and outlet valves. It is perhaps possible to reduce the unrestrained surfaces of the flexible bag with a pump having presser plates of the above-described type, but the forces acting on the presser plates rapidly reach several kilograms, thereby preventing the pump from operating unless very large amounts of energy are supplied.

An object of the invention is to provide a higher-performance implantable blood pump whose structure makes it possible to obtain non-displacement pump operation without requiring an additional compensation system.

SUMMARY OF THE INVENTION

More particularly, the present invention provides an implantable blood pump of the type comprising an outer shell, at least one essentially flat and deformable closed bag disposed inside the shell, having one of its walls in contact with the inside surface of said shell, and being connected to an inlet valve to enable it to be filled with blood fluid and to an outlet valve to enable it to deliver blood fluid, a cylindrical drum having an end edge of the bag fixed to a generator line thereof and organized to roll over the other wall of said bag, a C-shaped bracket mounted to rotate about the axis of said drum and having its central portion connected by means of a flexible inextensible component to the other end edge of the bag, and an electric motor integrated within the drum having its stator secured to said drum and having its rotor driving said bracket, said motor enabling the bracket and the drum to be driven in mutual and antagonistic rotation through a fraction of a turn to compress the bag which winds onto said drum in order to expel the blood fluid, wherein the outer shell is essentially rigid and constitutes a sealed housing in which the closed bag can deform, and by the fact that the closed bag is made, at least in part, of a material that is essentially inextensible in two directions so that the original inside volume of the bag remains constant regardless of its shape, said bag thus being made insensitive to external underpressure tending to increase its inside volume during blood fluid delivery.

In a particularly advantageous embodiment, the essentially inextensible material is a composite comprising a layer of polymer and two crossed sheets of fibers that are intimately bonded with the polymer.

It is then preferable for the two crossed sheets of fibers to be embedded in the layer of polymer; in a variant, the two crossed sheets of fibers constitute a screen glued externally on the surface of the polymer layer, or else internally on the surface of the polymer layer.

Also advantageously, the two crossed sheets of fibers are organized in two substantially orthogonal directions and/or extend diagonally relative to a direction parallel to the general direction of the drum axis. In particular, the two crossed sheets of fibers are disposed symmetrically about said direction parallel to the axis of the drum.

Preferably, the polymer layer is made of silicone or of polyurethane.

Also preferably, the fibers constituting at least one of the crossed sheets are synthetic fibers, or glass fibers, or carbon fibers.

It is also advantageous that the essentially inextensible material occupies at least a portion of the walls of the bag that does not remain in contact with the inside surface of the shell.

Also preferably, the bag constitutes a one-piece molded assembly.

Finally, it is advantageous for the essentially rigid outer shell to be made of carbon fibers.

BRIEF DESCRIPTION OF THE DRAWINGS

Embodiments of the invention are described by way of example with reference to the accompanying drawings, in which:

FIGS. 1 to 3 are partially cutaway views of an implantable pump of the invention;

FIGS. 4a to 4c are diagrammatic section views on line IV—IV of FIG. 2 illustrating the operation of the implantable pump and showing the zones of the closed bag that are subjected to a suction force during the ejection stage (FIG. 4c);

FIG. 5 is a larger scale view of a detail X in FIGS. 1 to 3, concerning the structure specific to the closed bag, and enabling two crossed sheets of fibers to be observed, with the fibers being embedded in the polymer layer in this case;

FIG. 6 is a section on VI—VI of FIG. 5; and

FIGS. 7 and 8 are sections analogous to that of FIG. 6, showing variants in which the fibers constitute a screen glued respectively on the outside or the inside surface of the layer of polymer.

DETAILED DESCRIPTION

An implantable blood pump 100 can be seen in FIGS. 1 to having a general structure that is as described in the Applicants' European patent No. 0 148 661, incorporated herein by reference.

The pump described is designed to provide ventricular assistance, for temporarily or definitively remedying failure of the left ventricle. Nevertheless, it will be understood that such a pump could easily be modified to provide a total heart prosthesis, by providing two associated ventricles each provided with its own valvules.

The pump is a peristaltic pump with non-displacement pump operation, i.e. it operates with blood being admitted at zero pressure or at a slightly negative pressure, thereby making it possible to avoid any risk of collapse in the event of insufficient venous drainage, and in addition, the absence of a moving member inside the bag guarantees a very low degree of hemolysis.

The implantable blood pump 100 includes an outer shell 110 in which an essentially flat and deformable closed bag 120 is disposed. The bag is made up of two walls 123 and 124 which are connected together at end edges 121 and 122, and which are outwardly extended by a bulging top portion 125 on which two connection tubes 131 and 141 are mounted, respectively containing an inlet valve 130 and an outlet valve 140 of conventional type (e.g. a flapping disk). The space inside the closed bag 110 is thus connected to the inlet valve 130 for being filled with blood fluid, and to the outlet valve 140 for delivering blood fluid. The "outside" wall 124 of the closed bag 120 makes contact with the inside surface of the shell 110, and it may be advantageous to secure it thereto by a spot of glue to limit motion of the system while in operation, by avoiding erratic movements inside the shell 110.

As described in greater detail below, the outer shell 110 is not flexible, nor is it flexible and reinforced by a metal mesh as is the case in the above-mentioned European patent, but it is essentially rigid so as to constitute a sealed housing in which the closed bag 120 can deform. It will be seen below that a special structure is provided for the bag 120, said structure making it possible to avoid the need to provide any kind of compensation system for opposing the above-mentioned under-pressure phenomenon which, when using a rigid outer shell, gives rise to a suction force on the closed bag during the ejection stage (delivering blood fluid).

The implantable pump 100 also includes a cylindrical drum 150 having one of the end edges (in this case the edge 121) of the bag 120 fixed on a generator line thereof, said drum being arranged to roll over the "inner" wall 123 of the said bag. A C-shaped bracket 160 is also provided which is rotatably mounted about the axis 151 of the drum 150, and whose central portion is connected by an inextensible flexible component 170 (in this case in the form of a sheet) to the other end edge (in this case the edge 122) of the closed bag 120.

An electric motor is integrally formed inside the drum 150 with the stator of the motor being secured to said drum and with its rotor driving the bracket 160, said motor enabling the bracket 160 and the drum 150 to be driven in mutual and antagonistic rotation through a fraction of a turn to compress the bag 120 which winds onto said drum, thereby expelling blood fluid.

It should be observed that the connection tubes 131 and 141 may also be disposed laterally (in a variant not shown), said disposition being favorable insofar as it coincides with the direction of peristaltic thrust and gives rise to reduced stress on the closed bag during displacement of the drum over the inner wall thereof.

FIGS. 1 and 3 also show the presence of a small link sheet 180 passing through a slot 161 in the middle portion of the C-shaped bracket 160, the edges of said sheet being fixed, e.g. by gluing, to the inside surface of the shell 110. Such a link sheet may facilitate good uniformity in the coupling between the shell and the bracket, however it is in no way essential for proper operation of the pump which is mounted in a manner that is intrinsically "floating", i.e. it is capable of operating without any external thrust point (as applies to the natural contractile bag), and this applies all the more in that the outer shell 110 is essentially rigid in the present case, and therefore provides good protection against external forces (e.g. compression of the chest).

FIGS. 4a, 4b, and 4c are diagrams showing how the implantable pump 100 operates.

This figure shows a magnetic sensor 190 disposed on the bracket 160, said sensor serving to detect the presence of magnets 191 and 192 carried by the drum 150 and disposed to correspond to two extreme positions of the fraction of a turn through which the mutual and antagonistic rotation is possible. Nevertheless, it is clear that this merely an example and that any other equivalent angle-identifying means, e.g. electronic means, could be used.

FIG. 4a corresponds to the filling stage (diastole). During this stage, the bracket 160 moves down to the left (in the figure) and the sheet 170 relaxes while the stator of the motor (the drum 150) reverses over the inner wall 123 of the bag 120. When the bracket 160 reaches its magnetic abutment, the direction of motor rotation is reversed.

The compression phase then begins, and FIG. 4b corresponds to an intermediate situation during said compression stage. The drum 150 rolls over the inner wall 123 of the bag 120 while bearing against the bracket 160 which moves relatively little. The bag 120 is compressed and the resistance felt by the motor becomes large preventing the drum 150 from moving. Subsequently, the drum 150 and the bracket 160 follow motion of least resistance, adapting themselves automatically at all times so as to bring into equilibrium the compression reaction of the bag 120 on the drum 150 with the traction reaction on the sheet 170.

FIG. 4c corresponds to the ejection stage (systole). During this stage, the bracket 160 secured to the rotor of the motor moves more quickly than during the filling stage and it reverses the lever arm. The stator (drum 150) is thrust against the bag 120, thereby assisting the bracket 160 in emptying said bag (although not completely in order to avoid a hemolysis phenomenon, i.e. in order to protect red corpuscles).

It should be observed that, in fact, the absolute displacement of the drum 150 inside the shell 110 is very small since it is mainly the bag 120 that is wound onto the drum (either directly or by bringing the end edge 122 towards the drum), unlike conventional peristaltic pumps used for pumping outside the body in which case the deformable cavity does not move.

The filling stage then takes place by the assembly returning to its initial position, with this return being the result simultaneously of venous pressure, the bag's own elasticity, and a command applied to the motor to assist this return stage.

FIG. 4c makes it easy to understand that if the outer shell 110 is rigid and constitutes a sealed housing, then free portions of the closed portion 120 that are not in contact with the outside surface of the drum or the inside surface of the rigid shell 110, i.e. nearly all of the outer wall 124 and the end portion of the inner wall 123 uncovered by the drum 150, are subjected to a suction force during the ejection stage. Although lower than the underpressure force encountered using a presser plate pump of the type mentioned above since the stress due to the underpressure applies progressively only to an area of the bag that becomes relatively small at the end of ejection, this underpressure force nevertheless still exists with its known drawbacks for the patient, and it must be countered.

This is where an essential characteristic of the invention applies, whereby the closed bag 120 is essentially inextensible in two directions over at least a portion thereof (i.e. at least in said unrestrained portions), such that the original inside volume of the bag 120 remains constant regardless of its shape, said bag thus being made insensitive to internal underpressure that would otherwise tend to increase its inside volume during delivery of blood fluid.

FIG. 4c makes this notion of constant original inside volume clear: it reduces to ensuring that the bag 120 has a constant perimeter (in cross-section, with the perimeter being the perimeter of the closed curve defined in section by said bag).

This measure makes it possible to oppose the suction phenomenon effectively and very simply: by avoiding any undesirable inflation of the bag, particularly in its critical portion situated between its connection to the inextensible flexible component and the drum, it is quite certain that the closed bag cannot increase its volume because of an underpressure effect. It is clear that in the absence of this special structure, the bag would deform, at least in the above-specified critical portion thereof, which would increase the residual volume corresponding to a non-ejected volume, thereby reducing the throughput of the pump, and the severe consequences that would result therefrom for the patient.

In a preferred embodiment, the essentially inextensible material constituting the closed bag 120, or at least those portions thereof which are unrestrained during the ejection stage, is a composite constituted by a layer of polymer and two crossed sheets of fibers that are intimately bound to the polymer.

FIG. 5 and the associated section of FIG. 6 show a fragment X of the closed bag 120 made in accordance with this special structure.

There can thus be seen a layer 200 of polymer and two crossed sheets of fibers 201 and 202 that are intimately linked with the polymer.

The polymer may be silicone or polyurethane.

The fibers constituting the crossed sheets may be selected from textile fibers having sufficiently high traction strength (e.g. fibers made of the material sold under the trademark Dacron ® or of polytetrafluorethylene), or they may be glass fibers or carbon fibers, or fibers made of the material sold under the trademark Kevlar ®.

The fibers 201 and 202 are organized as two crossed sheets at respective angles a and b with a reference direction Z which is preferably chosen to be parallel to the general direction of the axis 151 of the drum 150.

The two crossed sheets 201 and 202 are advantageously organized in two orthogonal directions (a+b=90°) that extend diagonally relative to the direction Z, and that are preferably symmetrical about said direction Z.

The two crossed sheets 201 and 202 may thus constitute a strong screen embedded in the layer of polymer 200, as shown in FIG. 6.

In a variant, the screen may be glued externally on the surface 204 of the layer of polymer (FIG. 7), or else internally on the surface 205 of said layer (FIG. 8); nevertheless, the internal solution appears to be of lower performance since it runs the risk of breaking red corpuscles (the risk of hemolysis). The surface state is equalized by using an appropriate glue that forms a bonding film 203: it is preferable to use a silicone glue.

In practice, it is advantageous to make the bag by molding so that it constitutes a single-piece molded assembly. Naturally, precautions will be taken to ensure that the bag has a minimum unrestrained area at the end of compression by designing a bag whose area is less than that of the system for compressing the peristaltic volume.

Similar materials but only having one sheet of parallel fibers have already been used for their mechanical strength in the medical field and with success, e.g. for constituting an artificial peritoneum: however, in that particular application, the objective was merely to achieve high mechanical strength to support the weight of the organs. Nevertheless, such materials having one or two screens but with fibers in one direction only are naturally deformable in all directions other than the fiber direction, such that they cannot "block" elasticity towards the outside for the purpose of preserving a "constant perimeter" around a closed curve, as is to be expected given that this problem does not arise with an artificial peritoneum.

The rigid outer shell forming the sealed housing is preferably made using a carbon fiber structure.

The invention obtains very significant advantages since it makes it possible to avoid providing any additional compensation system while nevertheless retaining the advantages of a rigid hermetically sealed shell, and while not giving rise to any significant increase in the electrical power required for driving the pump.

The invention is not limited to the embodiment described above, but on the contrary it covers any variant that uses equivalent means to reproduce the essential characteristics specified above.

We claim:

1. An implantable blood pump of the type comprising an outer shell, at least one essentially flat and deformable closed bag disposed inside the shell, having one of its walls in contact with the inside surface of said shell, and being connected to an inlet valve to enable it to be filled with blood fluid and to an outlet valve to enable it to deliver blood fluid, a cylindrical drum having an end edge of the bag fixed to a generator line thereof and organized to roll over the other wall of said bag, a C-shaped bracket mounted to rotate about the axis of said drum and having its central portion connected by means of a flexible inextensible component to the other end edge of the bag, and an electric motor integrated within the drum having its stator secured to said drum and having its rotor driving said bracket, said motor enabling the bracket and the drum to be driven in mutual and antagonistic rotation through a fraction of a turn to compress the bag which winds onto said drum in order to expel the blood fluid, wherein the outer shell is essentially rigid and constitutes a sealed housing in which the closed bag can deform, the closed bag being made, at least in part, of a material that is essentially inextensible in two directions so that the original inside volume of the bag remains constant regardless of its shape, said bag thus being made insensitive to external underpressure tending to increase its inside volume during blood fluid delivery.

2. A blood pump according to claim 1, wherein the essentially inextensible material is a composite comprising a layer of polymer and two crossed sheets of fibers that are intimately bonded with the polymer.

3. A blood pump according to claim 2, wherein the two crossed sheets of fibers are embedded in the layer of polymer.

4. A blood pump according to claim 2, wherein the two crossed sheets of fibers constitute a screen glued externally on the surface of the polymer layer.

5. A blood pump according to claim 2, wherein the two crossed sheets of fibers constitute a screen glued internally on the surface of the layer of polymer.

6. A blood pump according to claim 2, wherein the two crossed sheets of fibers are organized in two substantially orthogonal directions.

7. A blood pump according to claim 2, wherein the two crossed sheets of fibers extend diagonally relative to a direction parallel to the general direction of the axis of the drum.

8. A blood pump according to claim 7, wherein the two crossed sheets of fibers are disposed symmetrically about said direction parallel to the axis of the drum.

9. A blood pump according to claim 2, wherein the polymer layer is made of silicone or of polyurethane.

10. A blood pump according to claim 2, wherein the fibers constituting at least one of the crossed sheets are synthetic fibers.

11. A blood pump according to claim 2, wherein the fibers constituting at least one of the crossed sheets are glass fibers.

12. A blood pump according to claim 2, wherein the fibers constituting at least one of the crossed sheets are carbon fibers.

13. A blood pump according to claim 1, wherein the essentially inextensible material occupies at least a portion of the walls of the bag that does not remain in contact with the inside surface of the shell.

14. A blood pump according to claim 1, wherein the bag constitutes a one-piece molded assembly.

15. A blood pump according to claim 1, wherein the essentially rigid outer shell is made of carbon fibers.

* * * * *